(12) United States Patent
Liu

(10) Patent No.: US 12,125,666 B2
(45) Date of Patent: Oct. 22, 2024

(54) APPARATUS AND METHOD FOR GENERATING PARTICLE WAVE CARRYING ELECTRIC CHARGE

(71) Applicant: Yanbing Liu, Shandong (CN)

(72) Inventor: Yanbing Liu, Shandong (CN)

(*) Notice: Subject to any disclaimer, the term of this patent is extended or adjusted under 35 U.S.C. 154(b) by 311 days.

(21) Appl. No.: 17/774,148

(22) PCT Filed: Dec. 14, 2020

(86) PCT No.: PCT/CN2020/136194
§ 371 (c)(1),
(2) Date: May 4, 2022

(87) PCT Pub. No.: WO2021/089058
PCT Pub. Date: May 14, 2021

(65) Prior Publication Data
US 2022/0392733 A1 Dec. 8, 2022

(30) Foreign Application Priority Data

Nov. 4, 2019 (CN) .......................... 201911067751.4
Dec. 31, 2019 (CN) .......................... 201911421705.X

(51) Int. Cl.
*H01J 37/147* (2006.01)
*H01J 37/24* (2006.01)
*H03F 1/02* (2006.01)

(52) U.S. Cl.
CPC ...... *H01J 37/1471* (2013.01); *H01J 37/1472* (2013.01); *H01J 37/241* (2013.01); *H03F 1/0211* (2013.01)

(58) Field of Classification Search
CPC .. H01J 37/1471; H01J 37/1472; H01J 37/241; H01J 37/147; H03F 1/0211; H03F 3/50; H01T 23/00; A61N 1/44
See application file for complete search history.

(56) References Cited

U.S. PATENT DOCUMENTS

| 8,564,924 B1* | 10/2013 | Waddell | ............... | H01J 27/022 |
| | | | | 361/231 |
| 2002/0003215 A1* | 1/2002 | Berrian | ............... | H01J 37/3171 |
| | | | | 250/492.3 |

(Continued)

FOREIGN PATENT DOCUMENTS

| CN | 1924426 | 3/2007 |
| CN | 101637618 | 2/2010 |

(Continued)

OTHER PUBLICATIONS

"International Search Report (Form PCT/ISA/210) of PCT/CN2020/136194", mailed on Mar. 17, 2021, with English translation thereof, pp. 1-4.

*Primary Examiner* — David E Smith
*Assistant Examiner* — Christopher J Gassen
(74) *Attorney, Agent, or Firm* — Westbridge IP LLC

(57) ABSTRACT

A method and an apparatus for generating a particle wave carrying an electric charge is provided. The method comprises: on the basis of waveform information pre-stored in a waveform storage module, generating a corresponding digital waveform signal; the waveform information comprising amplitude and phase; on the basis of a digital-to-analog conversion module connected to the waveform storage module, converting the digital waveform signal having a pre-set phase into an analog waveform signal; on the basis of a power amplification module connected to the digital-to-analog conversion module, performing power amplification on the analog waveform signal; on the basis of a high-voltage generator connected to the power amplification module, performing high-voltage amplification on the power signal of the analog waveform signal; and by means of a quasi-continuous emission electrode connected to the high- (Continued)

voltage generator, emitting a charged particle wave on the basis of the analog waveform voltage signal.

16 Claims, 4 Drawing Sheets

(56) References Cited

U.S. PATENT DOCUMENTS

| | | | | |
|---|---|---|---|---|
| 2008/0232021 A1* | 9/2008 | Gefter | ................ | H01T 23/00 |
| | | | | 361/213 |
| 2014/0241462 A1* | 8/2014 | Bellaouar | ............ | H04B 1/0483 |
| | | | | 375/297 |
| 2015/0070812 A1* | 3/2015 | Lee | .................. | H01T 23/00 |
| | | | | 361/231 |
| 2016/0339261 A1* | 11/2016 | Mletzko | ................ | H05H 1/46 |
| 2017/0279412 A1* | 9/2017 | Afsahi | ................ | H03F 3/245 |

FOREIGN PATENT DOCUMENTS

| | | | | |
|---|---|---|---|---|
| CN | 101755519 | | 6/2010 | |
| CN | 105098606 | | 11/2015 | |
| CN | 109771825 | | 5/2019 | |
| CN | 111150936 | | 5/2020 | |
| JP | 2005328904 | | 12/2005 | |
| WO | WO-2004012212 A1 * | 2/2004 | ............ | H01F 13/00 |

* cited by examiner

APPARATUS AND METHOD FOR GENERATING PARTICLE WAVE CARRYING ELECTRIC CHARGE

CROSS-REFERENCE TO RELATED APPLICATION

This application is a 371 of international application of PCT application serial no. PCT/CN2020/136194, filed on Dec. 14, 2020, which claims the priority benefit of China application no. 201911421705.X, filed on Dec. 31, 2019 and China application no. 201911067751.4, filed on Nov. 4, 2019. The entirety of each of the above mentioned patent applications is hereby incorporated by reference herein and made a part of this specification.

TECHNICAL FIELD

The present invention relates to the technical field of space-charged particle generation, and in particular, to a method and an apparatus for generating a particle wave carrying an electric charge

BACKGROUND ART

The charged particles in the air include free electrons, negative oxygen ions, negative oxygen molecules and other negative ions that can move in short distances, wherein the negative oxygen ions in the air are generated under the action of high-voltage electrode corona or ultraviolet rays and can interact with the nerve endings on the skin surface, thereby improving the physiological functions of the human body.

DISCLOSURE OF THE INVENTION

The present particle wave generating apparatuses all use a high-voltage transformer to boost the power frequency voltage enough to make the dissociation energy obtained by the electrons on the surface of the metal electrode greater than the binding energy of the metal surface, the electrons will be separated from the surface of the metal electrode and move into space with sufficiently high kinetic energy; and moving electrons with kinetic energy collide with particles in the air (such as oxygen molecules, etc.), causing them to ionize and generate positive ions and negative ions. Wherein, positive ions are quickly captured by the negative high-voltage electrode, and electrons or negative ions will travel farther in the air under the repulsion of the negative high-voltage electrode. However, the charged negative ions move randomly in the air in the form of particles, rather than propagating through the air in the form of controlled waves. In particular, the charged particle generating apparatus involved cannot artificially control the intensity, the spatial density distribution and the spatial coverage of the charged particles emitted into the space, and due to the short transmission distance of the emitted particles, especially the small spatial solid angle and low spatial coverage, it cannot provide users with a better experience.

In order to solve the above-mentioned problems existing in the prior art, the present invention provides a method and an apparatus for generating charged particle waves, which are used for solving the problems that the present charged particle wave generating apparatus cannot control the time phase, intensity, spatial distribution density or spatial coverage of charged particle waves emitted into the space.

The specific technical scheme provided by the present invention is as follows:

an apparatus for generating charged particle waves, comprising: a charged particle wave control unit and a charged particle wave emission unit; the charged particle wave emission unit includes a high-voltage generator, a quasi-continuous emission electrode and an electric deflection device;

the high-voltage generator is connected to the charged particle wave control unit, and is adapted to perform high voltage control according to the waveform voltage signal output by the charged particle wave control unit; meanwhile, the high-voltage generator is also connected to the electric deflection device, and is adapted to control the electric deflection device to realize the maximum solid angle spatial scanning in the horizontal and vertical directions alternately and synchronously;

the quasi-continuous emission electrode is connected to the high-voltage generator, and is adapted to emit particle waves of corresponding density according to the received waveform voltage signal;

the electrical deflection device is connected to the quasi-continuous emission electrode, and is adapted to alternately control the vertical and horizontal propagation directions of the charged particle wave emitted by the quasi-continuous emitter electrode.

Preferably, the charged particle wave control unit comprises:

a waveform storage module, adapted to generate a corresponding digital waveform signal according to the pre-stored waveform information;

a digital-to-analog conversion module, connected to the waveform storage module, and adapted to convert the digital waveform signal into an analog waveform signal; and a power amplification module, connected to the digital-to-analog conversion module, and adapted to amplify the power of the analog waveform signal.

Preferably, the power amplification module comprises a voltage amplifier;

the voltage amplifier, connected to the digital-to-analog conversion module; and the base of the triode is connected to the voltage amplifier, the collector of the triode is connected to a power supply, and the emitter of the triode is connected to the high-voltage generator.

Preferably, the electric deflection device is positioned on one side of the quasi-continuous emission electrode emitting particle waves; and the electric deflection device comprises a vertical voltage waveform high-voltage electrode plate group and a horizontal voltage waveform high-voltage electrode plate group, and the vertical voltage waveform high-voltage electrode plate group is set in the vertical direction while the horizontal voltage waveform high-voltage electrode plate group is set in the horizontal direction; meanwhile, the vertical voltage waveform high-voltage electrode plate group and the horizontal voltage waveform high-voltage electrode plate group are orthogonal to each other, and are both parallel to the axis of the quasi-continuous emission electrode emitting charged particles, and the vertical voltage waveform high-voltage electrode plate group and the horizontal voltage waveform high-voltage electrode plate group are respectively used for controlling the vertical and horizontal propagation directions of the charged particle wave; the electric deflection device can alternately act on the particle waves emitted by the quasi-continuous emission electrode through the pulsed electric fields between the vertical voltage waveform high-voltage electrode plate group and the horizontal voltage waveform high-voltage electrode plate group; and the propagation direction of the generated particle wave is changed by the alternating voltage waveform electric field of the vertical voltage waveform high-voltage electrode plate group and a horizontal voltage waveform high-voltage electrode plate group in the electric deflection device.

Preferably, the vertical voltage waveform high-voltage electrode plate group comprises two voltage waveform high-voltage electrode plates; the two voltage waveform high-voltage electrode plates are oppositely set and parallel to the axis of the charged particle wave emitted by the quasi-continuous emission electrode, and the distance from the voltage waveform high-voltage electrode plate to the quasi-continuous emission electrode is d1; and the horizontal voltage waveform high-voltage electrode plate group comprises two voltage waveform high-voltage electrode plates; the two voltage waveform high-voltage electrode plates are oppositely set and are parallel to the axis of the charged particle wave emitted by the quasi-continuous emission electrode; the distance from the voltage waveform high-voltage electrode plate to the quasi-continuous emission electrode is d2, and d1 is not equal to d2.

Preferably, the voltage waveform high-voltage electrode plate is a square electrode plate;

the two voltage waveform high-voltage electrode plates of the vertical voltage waveform high-voltage electrode plate group as well as those of the horizontal voltage waveform high-voltage electrode plate group, are both parallel to the central axis of the charged particle waves emitted by the quasi-continuous emission electrode, and the center line of the two voltage waveform high-voltage electrode plates of the vertical voltage waveform high-voltage electrode plate group as well as that of the horizontal voltage waveform high-voltage electrode plate group is perpendicular to the center axis of the quasi-continuous emission electrode in the direction of emitting charged particle waves.

Preferably, the vertical voltage waveform high-voltage electrode plate group is 5 cm away from the emitting end of the quasi-continuous emission electrode, and the horizontal voltage waveform high-voltage electrode plate group is 2-3 cm away from the emitting end of the quasi-continuous emission electrode.

Preferably, the quasi-continuous emission electrode is an annular quasi-continuous emission electrode, and the distance between the vertical voltage waveform high-voltage electrode plate group and the horizontal voltage waveform high-voltage electrode plate group in the electric deflection device is larger than the diameter of the annular quasi-continuous emission electrode.

Preferably, the charged particle wave emission unit further comprises a fan; the quasi-continuous emission electrode is located between the fan and the electric deflection device, and the center of the fan is located on the concentric axis of the quasi-continuous emission electrode and the electric deflection device; the plane of the fan is perpendicular to the concentric axis, and the fan is used for enlarging the spatial propagation distance and the spatial coverage of the charged particle wave emitted by the quasi-continuous emission electrode.

Compared with the prior art, the beneficial effects of the present invention are as follows:

The embodiment of the present invention provides a method and an apparatus for generating charged particle waves. The method comprises: generating a waveform signal according to the pre-stored waveform information with a pre-set time phase in the waveform storage module. Through the digital-to-analog conversion of the digital-to-analog conversion module, the power amplification of the analog waveform signal by the power amplifying module, and the high-voltage amplification by the high-voltage generator, finally the charged particle waves are emitted by the quasi-continuous emission electrode. Through this method, according to the user's needs, a specific waveform signal with a specific time phase and intensity can be pre-stored in the waveform storage unit, and the specific waveform signal can be read at high frequency and amplified, to control the intensity of the voltage signal of the high-voltage generator and be supplied to the quasi-continuous emission electrode at high frequency; and at the same time, a part of the voltage signal of the high-voltage generator is taken out and supplied to the electric deflection device of the charged particle wave emission unit, to control the electric deflection device with the quasi-continuous emission electrode in synchronization to realize the maximum solid angle spatial scanning in both horizontal and vertical directions, so as to realize the maximum spatial density and spatial coverage of the particle wave emitted by the quasi-continuous electrode, thereby meeting the requirements of different users for particle wave performance application.

In the present invention, the electric deflection device and the quasi-continuous emission electrode are connected in parallel with the high-voltage generator, the concentration of emitted particles is directly related to the number of quasi-continuous emission electrodes and the voltage, and the waveform density of the emitted charged particles is directly related to both the frequency of the reading waveform storage unit and the waveform voltage intensity of the high-voltage generator. Meanwhile, the deflection angle of the electrical deflection device is directly related to the waveform voltage supplied by the high-voltage generator. When the high-voltage generator outputs a relatively higher voltage, the concentration of charged particles emitted by the quasi-continuous emission electrode is relatively larger, meanwhile, the waveform electric field applied to the electric deflection device is also stronger, and the coverage of the particles in space is also larger. On the contrary, When the high-voltage generator outputs a relatively lower voltage, the concentration of charged particles emitted by the quasi-continuous emission electrode is smaller, and the corresponding electric field generated by the waveform voltage applied to the electrical deflection device is also weaker, the deflection angle is smaller, and the spatial coverage ratio is thus smaller. Therefore, in order to obtain a higher density of space-charged particles, the amplitude of the waveform voltage provided by the high-voltage generator should be sufficiently high, and vice versa. To obtain a large enough spatial coverage, the waveform voltage supplied by the high-voltage generator to the two sets of electrical deflection devices should be sufficiently high, so that the deflection angle of the electrical deflection devices can be larger and the spatial coverage of particles can be greater.

The two groups of corrugated high-voltage electrode plates in the electric deflection device of the present invention, are arranged one after the other in the direction perpendicular to each other. This arrangement can be more convenient for installation and save costs; at the same time, after the quasi-continuous electrode emits charged particles, the charged particles are first deflected vertically by the electric field generated by a set of vertically arranged waveform high-voltage electrode plates, and then making horizontal deflection by means of electric field produced by a set of horizontally-arranged waveform high-voltage electrode plates, which can achieve a large spatial coverage of the particles. Further, the two groups of waveform high-voltage electrodes arranged vertically and horizontally respectively in this application are alternately controlled by specific waveform voltage signals, that is, the two groups of waveform high-voltage electrodes can be selectively switched on or off as required.

In the present invention, the quasi-continuous emission electrode is an annular quasi-continuous emission electrode, which is used for emitting physiologically functional specific charged particle waves such as α waves, θ waves or δ waves, which have high-efficiency regulation effect on human physiology, and has strict specific physiological parameters and properties as well as extremely strict controllability.

The charged particle wave emission unit provided by the present invention can transmit the particle waves to a long distance due to the repulsion of the electric field generated by the waveform voltage, and in addition to the assisting effect of the wind of the fan, the charged particle waves can be propagated relatively farther in space. At the same time, it is ensured that the wind field is as uniform as possible, the waveform of the charged particles is kept unchanged as much as possible, and that the particle wave voltage signal of the quasi-continuous emission electrode and the scanning synchronous waveform voltage applied to the electrical deflection device are the key factors to maintain the waveform of the charged particle emitted into space.

DETAILED DESCRIPTION OF THE PREFERRED EMBODIMENTS

In order to make the purpose, technical scheme and advantages of the present application clearer, the technical scheme of the present application will be clearly and completely described below in conjunction with the specific embodiments of the invention and the corresponding drawings. Obviously, the described embodiments are only a part of the embodiments of the present application, but not all of the embodiments. Based on the embodiments in the present application, all other embodiments obtained by those ordinary skill in the art without creative effort fall within the protection scope of the present application.

Figure 1:
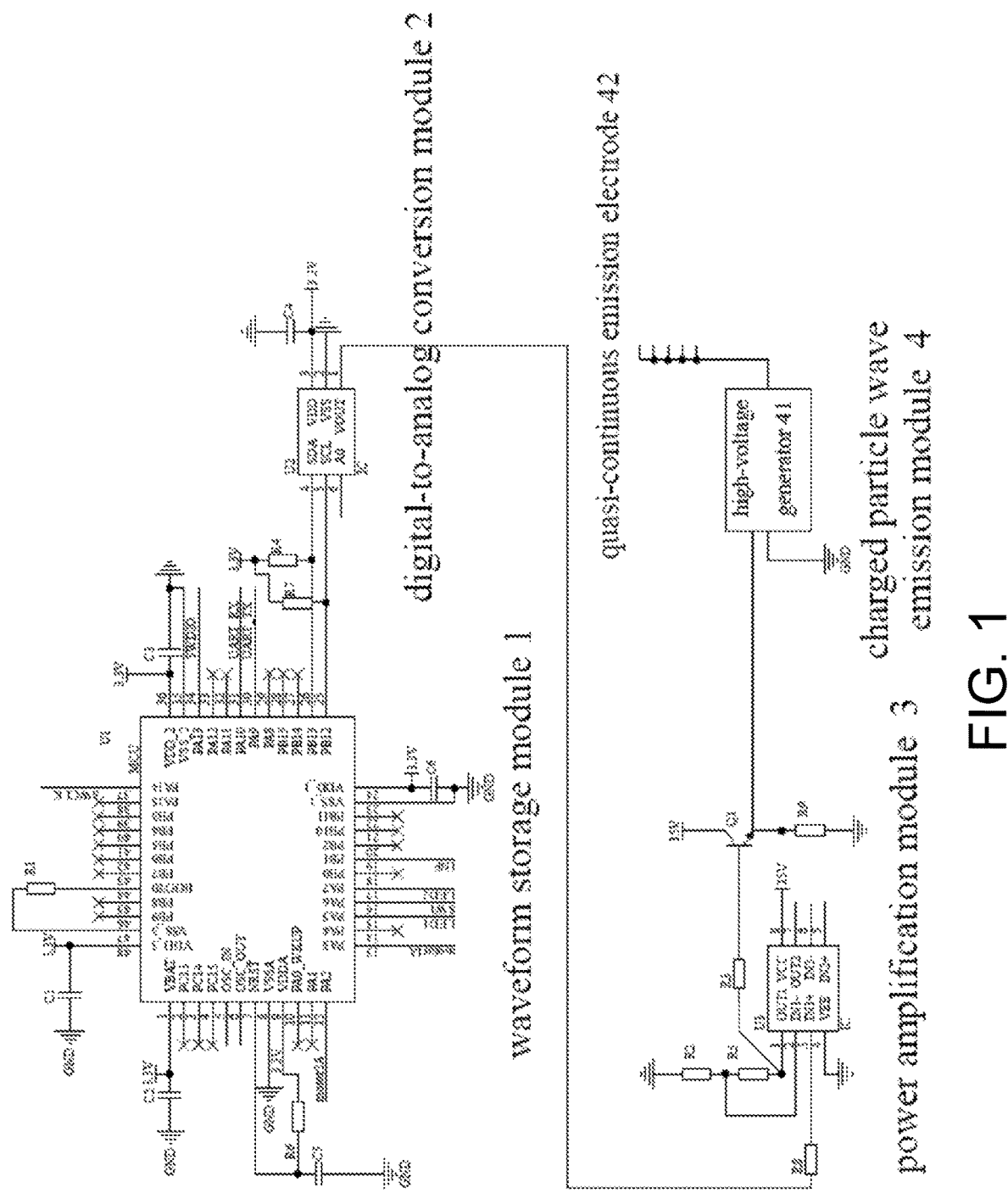
FIG. 1 is a schematic circuit diagram of a charged particle wave generating apparatus provided by the present embodiment.

FIG. 1 is a schematic circuit diagram of a charged particle wave generating apparatus provided by an embodiment of the present application; The circuit mainly comprises a waveform storage module 1, a digital-to-analog conversion module 2, a power amplification module 3 and a charged particle wave emission module 4, wherein the waveform storage module 1, the digital-to-analog conversion module 2, the power amplification module 3 and the charged particle wave emission module 4 are sequentially connected.

Figure 2:
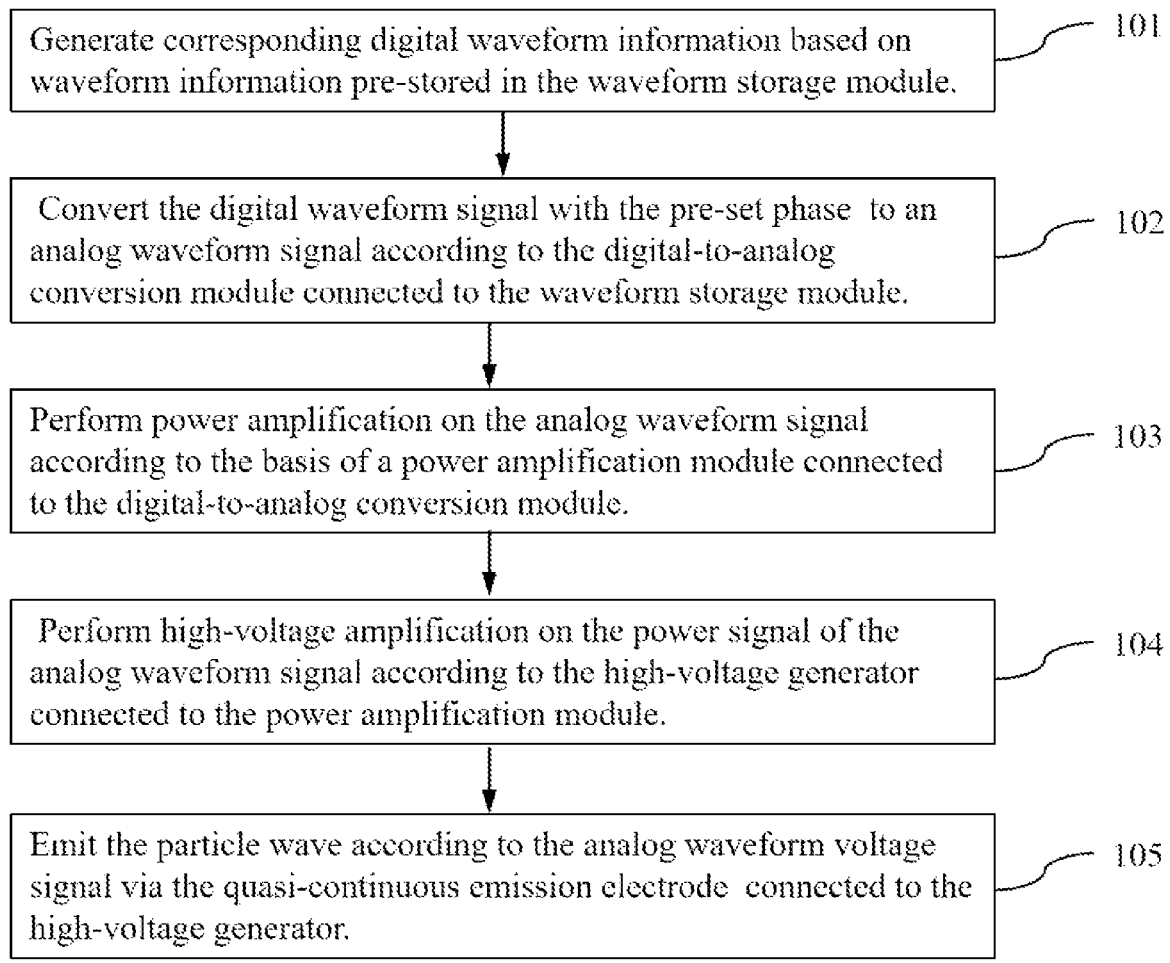
FIG. 2 is a flow chart of a charged particle wave generating method provided by the present embodiment.

FIG. 2 is a flow chart of a charged particle wave generating method provided by an embodiment of the present application, comprising:

S101: generating a corresponding digital waveform signal according to the pre-stored waveform information in the waveform storage module;

In the embodiment of the present application, corresponding digital waveform signals can be generated by the waveform storage module through the waveform information pre-stored in the waveform storage module.

As shown in FIG. 1, the waveform storage module 1 can be specifically a Microcontroller Unit (MCU), and several pins of the MCU may include program writing pins, and the program writing pins, which are connected to the memory (not shown in FIG. 1). After the programmer (not shown in FIG. 1) writes the pre-written program stored in the memory into the MCU via the program writing pins, the MCU can read the corresponding information and generate the corresponding digital waveform signal according to the waveform information included in the program, wherein the waveform information comprises the amplitude and time phase of the waveform. The time phase of the waveform represents the frequency of the waveform signal and the like.

Furthermore, a plurality of different voltage waveform information can be stored in the waveform storage module 1. The waveform storage module 1 can determine the waveform information selected by the user from the pre-stored voltage waveform information, and generates the corresponding digital waveform signal according to the user's selection.

Figure 3:
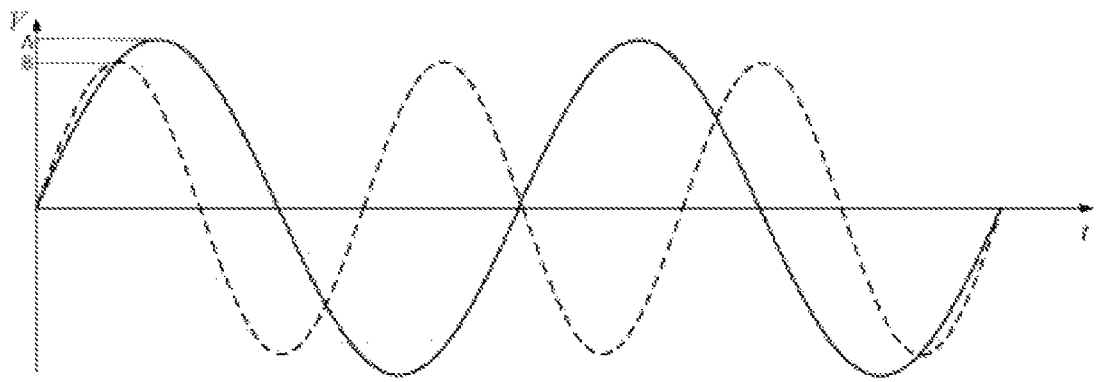
FIG. 3 is a schematic diagram of various waveform signals provided by the present embodiment.

As shown in FIG. 3, the solid line sine wave and the dashed line sine wave listed in the figure represent two different waveform signals respectively, and the amplitudes and time phases of which are different. Wherein the amplitude A of the solid line sine wave is higher than the amplitude B of the dashed line sine wave, and the time phase of the solid line sine wave is lower than the time phase of the dashed line sine wave.

In one possible implementation mode, the waveform storage module 1 can receive a selection instruction sent by a user through a remote controller or a control knob and determine the waveform information selected by the user according to the received selection instruction, so that the particle wave generating apparatus can be controlled to emit particle waves with different intensities and spatial densities.

S102: converting the digital waveform signal with a pre-set time phase into an analog waveform signal according to the digital-to-analog conversion module connected with the waveform storage module.

In the embodiment of the invention, digital waveform signals sent by the waveform storage module can be converted into analog waveform signals through the digital-to-analog conversion module Specifically, as shown in FIG. 1, the digital-to-analog conversion module 2 is connected with the waveform storage module 1, and the digital-to-analog conversion module 2 can convert the digital waveform signal received from the waveform storage module 1 into an analog waveform signal, so that the particle waves can be output in the form of analog waveform signals.

S103: according to the power amplification module connected to the digital-to-analog conversion module, performing power amplification on the analog waveform signals.

In the embodiment of the present application, the analog waveform signal can be subjected to power amplification through the power amplification module so as to enhance the amplitude and frequency of the output analog waveform signals and enable the output analog waveform signals to be suitable for subsequent high-voltage power supplies.

As shown in FIG. 1, the power amplification module 3 is connected to the digital-to-analog conversion module 2; the power amplification module 3 specifically comprises a voltage amplifier and a triode; wherein, the voltage amplifier is connected to the digital-to-analog conversion module 2, and the base of the triode is connected to the voltage amplifier, the collector of the triode is connected to a power supply; and the emitter of the triode is connected to the charged particle wave emission module 4.

The voltage amplifier may be an amplifier chip, and one pin of the amplifier chip is connected to a power supply, which is usually suitable for lower voltages, such as 5V, etc. The voltage amplifier can enlarge the input voltage and output a higher voltage so that the output voltage can satisfy the voltage demand of the subsequent particle wave transmission device (i.e., the quasi-continuous emission electrode). Furthermore, by amplifying the output voltage, the amplitude of the analog waveform signal passed through the voltage amplifier will increase, and the intensity of the waveform is enhanced, wherein, the voltage amplifier can enlarge the voltage based on the fixed multiple.

The triode can amplify the passing current so as to increase the signal power and achieve the power required for driving the quasi-continuous emission electrode; Further, the amplification of the current by the triode can also generate an amplified power to the analog waveform signal, and the time phase of the analog waveform signal is increased, thereby increasing the spatial density of the output particle wave.

S104: according to the high-voltage generator connected to the power amplification module, performing high-voltage amplification on the power signal of the analog waveform signals.

S105: emitting the particle wave according to the analog waveform signal via a quasi-continuous emission electrode connected to the high-voltage generator.

As shown in FIG. 1, in the embodiment of the present application, the charged particle waves can be emitted through the charged particle wave emission module 4.

Specifically, the charged particle wave emission module 4 may include a high voltage generator 41 and a quasi-continuous emission electrode 42. The digital-to-analog conversion module 2, which is amplified by the power amplifier module 2, controls the high-voltage generator 41 to provide high voltage for emitting particle waves to the quasi-continuous emission electrode 42, from which the particle waves with corresponding waveforms are emitted into the air.

In the embodiment of the application, the waveform storage module 1 can generate a digital waveform signal according to the pre-stored waveform information, and the digital waveform signal is subjected to digital-to-analog conversion of the digital-to-analog conversion module 2 and power amplification of the power amplification module 3, and finally charged particle waves are emitted through the charged particle wave emission module 4.

The charged particle wave generating apparatus enables charged particles in the air to have wave properties, forming charged particle waves. The particle wave generator can regulate and control the high voltage output of high voltage power supply by selecting pre-set waveform signals with several kinds of time phases and amplitude parameters, to ensure the emission of charged particles in quasi-continuous emission electrode and make the time phases, amplitudes and particle wave densities of charged particle waves in the air change correspondingly.

In the present scheme, the waveform storage module can determine the waveform information selected by the user from several different waveform information, and the particle wave generating apparatus can generate particle waves with corresponding time phase, intensity and spatial density distribution, which provides multiple choices for users. The user can freely control the time phase, the strength and the spatial density distribution of the particle wave according to the user's needs, so that the particle wave generating apparatus provided by the scheme has higher flexibility, adjustability and wider applicability.

This scheme uses the pre-set time phase and other waveform parameters stored in the waveform storage module to amplify the power of the waveform signal by the power amplification module, which can further conveniently and accurately adjust the time phase, amplitude and spatial density distribution of the particle wave generated by the quasi-continuous emission electrode, in order to control the generation of particle wave intensity and spatial density distribution in needs, and the charged particle wave in the space with the phase, vibration and density of the high spatial density distribution required by the user can be realized, so as to improve the user's experience.

Figure 4A:
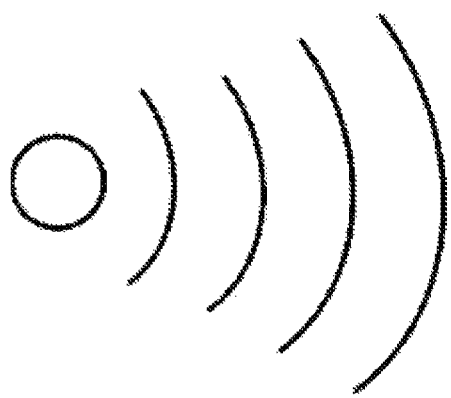
FIG. 4A and FIG. 4B are schematic diagrams of different particle waves generated by different waveform signals corresponding to FIG. 3 provided in this embodiment, respectively.
Figure 4B:
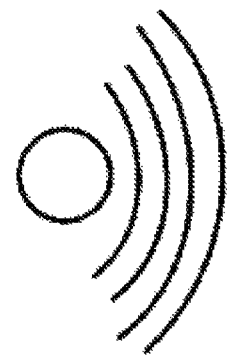

As shown in FIG. 4A and FIG. 4B, a schematic diagram showing different particle waves generated by the charged particle wave generating apparatus. Among them, the circle in FIG. 4A and FIG. 4B represents a particle wave generating apparatus, and the arcuate curve in the figure represents a schematic diagram of the wavefront of the propagating particle wave, and the distance between the wavefront represents the spatial density distribution of the particle wave. As can be seen from the corresponding schematic diagram 3, FIG. 4A represents the particle wave corresponding to the solid line sine wave of FIG. 3, which has a relatively high intensity and a relatively low density distribution, while FIG. 4B represents the particle wave corresponding to the dashed line sine wave of FIG. 3, which has a relatively weak intensity and a relatively high density distribution.

In addition, by pre-storing different waveform information in the waveform storage module, when a user controls the particle wave generating apparatus to generate different particle waves, the user can directly send out instruction to call out the corresponding waveform information from the waveform storage module to implement switch of particle waves with different waveforms. So that there is no need to modify the stored waveform information, simple in construction, easy and simple to operate. Also, through several pre-stored waveform information, it's fully considered of the demands of different users and different waveform information can be set up in order to meet different users' needs for charged particle wave function of different parameters, enable users to control and regulate freely to produce different particle waves as needed.

Figure 5A:
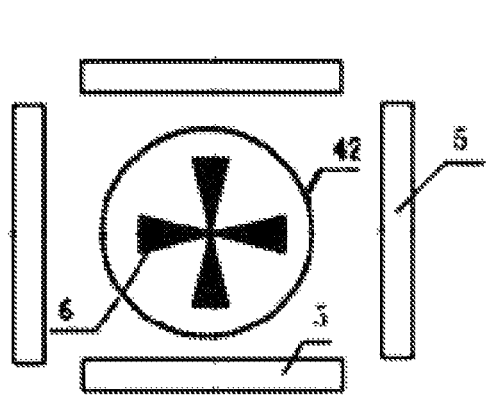
FIG. 5A is a schematic diagram of the front structure of the charged particle wave generating apparatus provided in this embodiment.
Figure 5B:
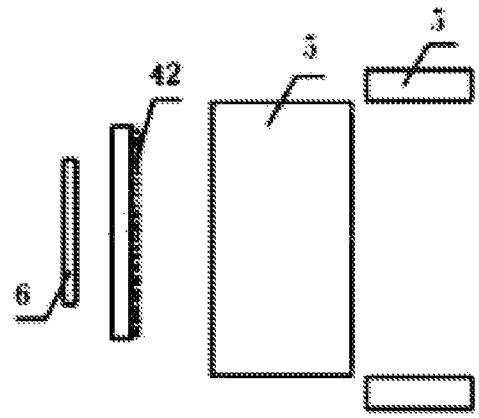
FIG. 5B is a schematic diagram of the side structure of the charged particle wave generating apparatus provided in this embodiment.

FIG. 5A and FIG. 5B are schematic diagrams of front and side structures of the charged particle wave generating apparatus provided in the embodiment of the present application, respectively. As shown in FIG. 5A and FIG. 5B, the particle wave generating apparatus includes a quasi-continuous emission electrode 42, an electric deflection device 5 and a fan 6. The quasi-continuous emission electrode 42 is located between the fan 6 and the electric deflection device 5, and the center of the fan 6 is located on the concentric axis of the quasi-continuous emission electrode 42 and the electric deflection device 5, meanwhile, the plane of the fan 6 is perpendicular to the concentric axis, and the fan 6 is used for enlarging the spatial propagation distance and spatial coverage of the charged particle wave emitted by the quasi-continuous emission electrode 42.

The electric deflection device 5 comprises two sets of waveform high-voltage electrode plates with the same size externally connected to the high-voltage generator, each group of waveform high-voltage electrode plates consists of two same waveform high-voltage electrode plates which are opposite and parallel, and the two sets of waveform high-voltage electrode plates are respectively vertically up and down arranged at the front end of the quasi-continuous emission electrode 5 in the direction of emitting charged particle waves.

The electric deflection device can alternately act on the particle waves emitted by the quasi-continuous emission electrode through the waveform electric fields between the 2 sets of waveform high-voltage electrode plates, so that deflecting the propagation direction of the particle waves to achieve a wider spatial coverage. Through changing the propagation direction of the emitted particle wave by the two groups of alternately changed waveform electric field in the electric deflection device, the larger spatial coverage is realized, and the utilization is improved, and the particle wave generating apparatus can emit the particle wave in the most suitable use mode according to the use habits of human bodies, and facilitate the user's operation.

When the user uses the particle wave generating apparatus, the particle wave emitting spatial angle can be controlled by adjusting the strength of the two sets of waveform high-voltage electric fields in the electrical deflection device, so that the wide coverage of charged particle waves in the space can be realized, and different requirements of the users can be met.

In one embodiment, the quasi-continuous emission electrode 42 may be annular or otherwise shaped, and the electric deflection device 5 is composed of two sets of square-wave-shaped high-voltage electrode plates which are vertically and adjacently arranged up and down and connected to the waveform high-voltage generator 41. The two sets of waveform high-voltage electrode plates are parallel to the central axis of the annular quasi-continuous emission electrode, and the central line of each set of waveform high-voltage electrode plates is perpendicular to the central axis of the annular quasi-continuous emission electrode. Fix the waveform high-voltage electrode plates near the annular quasi-continuous emission electrode and are about 5 cm from the transmitting end of the quasi-continuous emission electrode.

The particle wave emitted by the annular quasi-continuous emission electrode will propagate outwards through the two sets of waveform high-voltage electrode plates arranged up and down. When the charged particle wave passes through the alternately changed electric field in the two sets of waveform high-voltage electrode plates of the electric deflection device, which are parallel to the central axis of the annular quasi-continuous emission electrode, the charged particle wave propagates along the vertical and horizontal directions under the action of alternately changed electric field under the control of the waveform electric field, and the user can control the size of the particle wave emitting spatial angle by controlling the alternately changed waveform voltage according to the requirement, thereby realizing a large space coverage of the charged particle wave, and improving the demand of users for greater use of efficacy of the device.

The center of the fan 6 is located on the concentric axis of the annular quasi-continuous emission electrode and the two sets of electric deflection devices, and the plane of the fan is perpendicular to the concentric axis, and the fan is provided at a distance of about 2 cm at the back end edge of the annular quasi-continuous emission electrode. The two sets of voltage waveform plates in the electric deflection device are slightly larger than the diameter of the annular quasi-continuous emission electrode, and the two sets of voltage waveform high-voltage electrode plates in the electric deflection device are arranged at the position about 5 cm away from the front end of the emitting particle direction of the annular quasi-continuous emission electrode. When the particle wave emitted by the annular quasi-continuous emission electrode propagates outwards, it is deflected via alternately varying voltage waveform electric field in the electric deflection device controlled by the waveform high voltage, thereby achieving a large coverage of space.

By adjusting the waveform voltage, users can freely control the transmission distance and space coverage of particle waves. On the other hand, through the setting of the noiseless fan, it is easy to make the space propagation of charged particle waves propagated in the space travel farther, so that the users' experience is improved.

In addition, in FIG. 1, the waveform storage module 1 is provided with 48 pins. And Pin 1 is connected with a capacitor C2, which is grounded; Pin 7 is connected with a resistor R6, which is also connected with Pin 9, and Pin 7 is also connected with a capacitor C5, which is grounded; Pin 24 is connected with a capacitor C6, and the capacitor C6 is also connected with Pin 23 and ground respectively; Pin 36 is connected with a capacitor C3, and the capacitor C3 is also connected with Pin 35 and ground respectively; Pin 44 is connected with a resistor R1, which is also connected with Pin 47; Pin 48 is connected with a capacitor C1, which is also grounded; Pin 1, Pin 24, Pin 36 and Pin 48 are respectively connected with the power supply end.

The Pin 12 and Pin 13 of the waveform storage module 1 are the fan pins, Pin 15 and Pin 17 are the LED indicator lamp pins, Pin 16 is the control key pin of the particle wave generating apparatus, Pin 19 is the remote controller pin, Pin 30 and Pin 31 are the serial port pins, and Pin 34 and Pin 37 are the program writing pins.

The digital-to-analog conversion module 2 is provided with 6 pins, the waveform storage module 1 is respectively connected with Pin 4 and Pin 5 of the digital-to-analog conversion module 2 through Pin 25 and Pin 26, and Pin 25 of the waveform storage module 1 is connected with a resistor R7, Pin 26 of the waveform storage module 1 is connected with a resistor D4, and the resistor R7 is connected with the resistor R4, and Pin 25 and Pin 26 of the waveform storage module 1 are respectively connected with a power supply end.

Pin 2 of the digital-to-analog conversion module 2 is grounded, Pin 3 of the digital-to-analog conversion module 2 is connected with a capacitor C4, and the capacitor C4 is grounded, Pin 3 of the digital-to-analog conversion module 2 is also connected with a power supply end, Pin 1 of the digital-to-analog conversion module 2 is connected with a resistor R8, and the resistor R8 is connected with a power amplification module 3.

The voltage amplifier has eight pins, wherein Pin 8 is connected to the power supply, and Pin 4 is connected to the ground; Pin 2 is connected to a resistor R2 and the resistor R2 is grounded, meanwhile, Pin 2 is also connected to a resistor R5, and the resistor R5 is connected to Pin 1; Pin 1 is connected to a resistor R3, which is connected to the base of the triode.

The triode is connected to the high-voltage generator 41 and then grounded; The triode is of NPN type, and the collector of the triode is connected with a power supply, the emitter is connected with the high-voltage generator 41, the emitter is also connected with a resistor R9, and the resistor R9 is grounded.

Wherein the voltage value of the power supply end is 3.3 V, and the voltage value of the power source is 15V.

In one embodiment, the particle wave generating apparatus further comprises an indicator light, the indicator light can be used for indicating the working state of the particle wave generating apparatus, and the color of the specific indicator light and the corresponding expression meaning can be set as required, and the application does not limit the color and the corresponding expression meaning.

Figure 6:
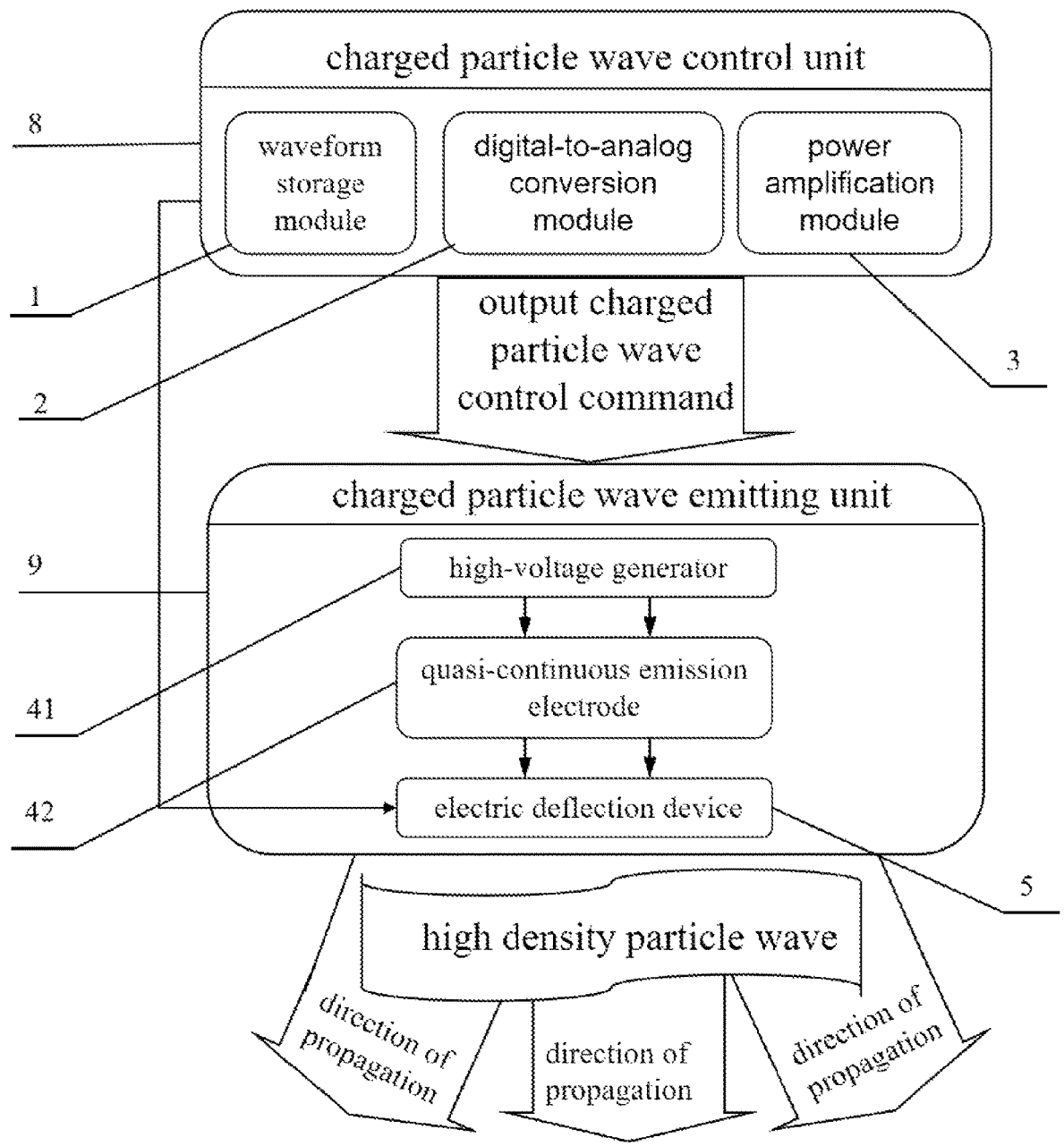
FIG. 6 is a schematic diagram of the working principle of the charged particle wave generating apparatus provided in this embodiment.

FIG. 6 is a schematic diagram of the operation of the charged particle wave generating apparatus provided by an embodiment of the present application.

As shown in FIG. 6, the particle wave generating apparatus comprises a charged particle wave control unit 8 and a charged particle wave emission unit 9. Wherein the charged particle wave control unit 8 comprises a waveform storage module 1, a digital-to-analog conversion module 2 and a power amplification module 3; and the charged particle wave emission unit 9 comprises a high-voltage generator 41, an annular quasi-continuous emission electrode 42 and an electric deflection device 5.

In the particle wave generating apparatus, the charged particle wave control unit 8 is used for controlling parameters such as time phase and amplitude of the particle waves, so as to control the time phase, strength, space density distribution and space coverage rate of the emitted particle waves. The charged particle wave emission unit 9 is used for emitting the particle waves with high density distribution and large space coverage rate with corresponding amplitudes and time phases according to the charged particle wave control commands of the charged particle wave control unit 8.

Specifically, the waveform storage module 1 is used for storing waveform information, wherein the waveform information comprises amplitudes and time phases parameters of particle waves. At the same time, the waveform storage module 1 can store a plurality of different waveform information so as to emit particle waves with different time phases and amplitudes.

The digital-to-analog conversion module 2 is used for D/A conversion of the received digital waveform signal and converting the digital waveform signal into a corresponding analog waveform signal so as to facilitate the output of the subsequent particle wave.

The power amplification module 3 is used for amplifying the power of the analog waveform signal by amplifying voltage, current and the like, so that the analog waveform signal can meet the voltage requirement of a subsequent particle wave emitting device. And after the power is amplified, the analog waveform signal can be enhanced in amplitude, time phase and the like.

The high-voltage generator 41 is connected to the quasi-continuous emission electrode 42 for emitting charged particle waves. To be specific, the corresponding high density charged particle waves are emitted by the high-voltage generator 41 according to the received analog waveform signals.

The high voltage generator 41 is connected to the electric deflection device 4 to control the electric deflection device 4 to realize the maximum solid angle space scanning both in the horizontal direction and the vertical direction.

The electric deflection device 5 is used for controlling the propagation direction of the particle wave emitted by the annular quasi-continuous emission electrode 42 and enlarging the space coverage by controlling the emitting direction of the high-density particle wave.

The electric deflection device is located on one side of the quasi-continuous emission electrode emitting particle waves. The electric deflection device comprises a vertical voltage waveform high-voltage electrode plate group and a horizontal voltage waveform high-voltage electrode plate group, and the vertical voltage waveform high-voltage electrode plate group is arranged in the vertical direction while the horizontal voltage waveform high-voltage electrode plate group is horizontally arranged, meanwhile, the vertical voltage waveform high-voltage electrode plate group and the horizontal voltage waveform high-voltage electrode plate group are mutually orthogonal to each other and are both parallel to the axis of charged particles emitted by the quasi-continuous emission electrode, and the vertical voltage waveform high-voltage electrode group and the horizontal voltage waveform high-voltage electrode plate group are respectively used for controlling the vertical and horizontal propagation directions of charged particle wave; The electric deflection device can act alternately on the particle wave emitted by the quasi-continuous emission electrode through the pulsed electric fields between the vertical voltage waveform high-voltage electrode group and the horizontal voltage waveform high-voltage electrode plate group; The propagation direction of the generated particle wave is changed by the alternating voltage waveform electric field of the vertical voltage waveform high-voltage electrode plate group and the horizontal voltage waveform high-voltage electrode plate group in the electric deflection device Specifically, the vertical voltage waveform high-voltage electrode plate group comprises two voltage waveform high-voltage electrode plates, and the two voltage waveform high-voltage electrode plates are arranged opposite to each other and parallel to the axis of the charged particle wave emitted by the quasi-continuous emission electrode, and the distance from the voltage waveform high-voltage electrode plate to the quasi-continuous emission electrode is d1; The horizontal voltage waveform high-voltage electrode plate group comprises two voltage waveform high-voltage electrode plates; the two voltage waveform high-voltage electrode plates are oppositely arranged and are parallel to the axis of the charged particle wave emitted by the quasi-continuous emission electrode, and the distance from the voltage waveform high-voltage electrode plate to the quasi-continuous emission electrode is d2; and d1 is not equal to d2.

The two voltage waveform high-voltage electrode plates of the vertical voltage waveform high-voltage electrode plate group as well as those of the horizontal voltage waveform high-voltage electrode plate group are parallel to the central axis of the charged particle wave emitted by the quasi-continuous emission electrode, and the central line of the two voltage waveform high-voltage electrode plates of the vertical voltage waveform high-voltage electrode plate group as well as that of the horizontal voltage waveform high-voltage electrode plate group is perpendicularly orthogonal to the central axis of the annular quasi-continuous emission electrode in the direction of emitting charged particle waves.

The vertical voltage waveform high-voltage electrode plate group is 5 cm away from the emitting end of the quasi-continuous emission electrode, and the horizontal voltage waveform high-voltage electrode plate group is 2-3 cm away from the emitting end of the quasi-continuous emission electrode.

The quasi-continuous emission electrode is an annular quasi-continuous emission electrode, and the distance between the vertical voltage waveform high-voltage electrode plate group and the horizontal voltage waveform high-voltage electrode plate group in the electric deflection device is greater than the diameter of the annular quasi-continuous emission electrode.

It is to be noted that the modules of FIG. 6 may correspond to the components of FIG. 1 described above, and as for the parts not detailed in this application embodiment, please refer to the relevant description in FIG. 1 above.

The above is only an embodiment of this application and is not intended to limit this application. For technical personnel in this field, this application can be subject to various modifications and changes. Any modifications, equivalent substitutions, modifications, etc., made within the spirit and principles of the present application, shall fall within the scope of claims in the present application.

What is claimed is:

1. An apparatus for generating a particle wave carrying electric charge, comprising: a charged particle wave control unit and a charged particle wave emission unit, the charged particle wave emission unit comprises a high-voltage generator, an emission electrode and an electric deflection device, the high-voltage generator is connected to the charged particle wave control unit, and is adapted to perform high-voltage control according to a waveform voltage signal output by the charged particle wave control unit, the high-voltage generator is connected to the electric deflection device, and is adapted to control the electric deflection device to realize a solid angle spatial scanning in a horizontal direction and a vertical direction alternately and synchronously, the emission electrode is connected to the high-voltage generator, and is adapted to emit a charged particle wave of corresponding density according to the waveform voltage signal received, the electric deflection device is connected to the emission electrode, and is adapted to alternately control a vertical propagation direction and a horizontal propagation direction of the charged particle wave emitted by the emission electrode, wherein the charged particle wave control unit comprises:

a waveform storage module, adapted to generate a digital waveform signal correspondingly according to a pre-stored waveform information;

a digital-to-analog conversion module, connected to the waveform storage module, and adapted to convert the digital waveform signal into an analog waveform signal; and a power amplification module, connected to the digital-to-analog conversion module, and adapted to amplify a power of the analog waveform signal, wherein the power amplification module comprises a voltage amplifier and a triode, the voltage amplifier is connected to the digital-to-analog conversion module, a base of the triode is connected to the voltage amplifier, a collector of the triode is connected to a power source, and an emitter of the triode is connected to the high-voltage generator, wherein the electric deflection device is disposed on one side of the emission electrode emitting the charged particle wave, wherein the one side is a side of the emission electrode that is configured to emit the charged particle wave, the electric deflection device comprises a vertical voltage waveform high-voltage electrode plate group and a horizontal voltage waveform high-voltage electrode plate group, the vertical voltage waveform high-voltage electrode plate group is set in the vertical direction while the horizontal voltage waveform high-voltage electrode plate group is set in the horizontal direction, the vertical voltage waveform high-voltage electrode plate group and the horizontal voltage waveform high-voltage electrode plate group are orthogonal to each other, and are both parallel to an axis of the charged particle emitted by the emission electrode, the vertical voltage waveform high-voltage electrode plate group and the horizontal voltage waveform high-voltage electrode plate group are respectively configured to control the vertical propagation direction and the horizontal propagation direction of the charged particle wave;

the electric deflection device alternately acts on the charged particle wave emitted by the emission electrode through a pulsed electric field between the vertical voltage waveform high-voltage electrode plate group and the horizontal voltage waveform high-voltage electrode plate group; and a propagation direction of the charged particle wave generated is changed by an alternating voltage waveform electric field of the vertical voltage waveform high-voltage electrode plate group and the horizontal voltage waveform high-voltage electrode plate group in the electric deflection device.

2. The apparatus for generating the particle wave carrying electric charge according to claim 1, wherein the vertical voltage waveform high-voltage electrode plate group comprises two voltage waveform high-voltage electrode plates, the two voltage waveform high-voltage electrode plates are oppositely set and parallel to the axis of the charged particle wave emitted by the emission electrode, a distance from the two voltage waveform high-voltage electrode plates of the vertical voltage waveform high-voltage electrode plate group to the emission electrode is d1, the horizontal voltage waveform high-voltage electrode plate group comprises two voltage waveform high-voltage electrode plates; the two voltage waveform high-voltage electrode plates are oppositely set and are parallel to the axis of the charged particle wave emitted by the emission electrode, a distance from the two voltage waveform high-voltage electrode plates of the horizontal voltage waveform high-voltage electrode plate group to the emission electrode is d2, and d1 is not equal to d2.

3. The apparatus for generating the particle wave carrying electric charge according to claim 2, wherein each of the voltage waveform high-voltage electrode plate is a square electrode plate, the two voltage waveform high-voltage electrode plates of the vertical voltage waveform high-voltage electrode plate group and the two voltage waveform high-voltage electrode plates of the horizontal voltage waveform high-voltage electrode plate group are both parallel to a central axis of the charged particle wave by emitted by the emission electrode, and a center line respectively spanning between opposing faces of the two voltage waveform high-voltage electrode plates of the vertical voltage waveform high-voltage electrode plate group and the two voltage waveform high-voltage electrode plates of the horizontal voltage waveform high-voltage electrode plate group is perpendicular to a central axis of the emission electrode, the center line being disposed in the direction of the emitted the charged particle wave.

4. The apparatus for generating the particle wave carrying electric charge according to claim 3, wherein
the vertical voltage waveform high-voltage electrode plate group is 5 cm away from an emitting end of the emission electrode, and
the horizontal voltage waveform high-voltage electrode plate group is 2-3 cm away from the emitting end of the emission electrode.

5. The apparatus for generating the particle wave carrying electric charge according to claim 1, wherein
the emission electrode is an annular emission electrode, and
a distance between the vertical voltage waveform high-voltage electrode plate group and the horizontal voltage waveform high-voltage electrode plate group in the electric deflection device is larger than a diameter of the annular emission electrode.

6. The apparatus for generating the particle wave carrying electric charge according to claim 1, wherein
the charged particle wave emission unit further comprises a fan,
the emission electrode is located between the fan and the electric deflection device, and
a center of the fan is located on a concentric axis of the emission electrode and the electric deflection device; the plane of the fan is perpendicular to the concentric axis, and the fan is configured to enlarge a spatial propagation distance and a spatial coverage of the charged particle wave emitted by the emission electrode.

7. A method for generating a particle wave carrying electric charge, comprising:
performing a high-voltage amplification of a power signal of an analog waveform signal based on a high-voltage generator connected to a charged particle wave control unit;
emitting a charged particle wave based on the analog waveform signal via an emission electrode connected to the high-voltage generator;
alternately and synchronously controlling an electric deflection device to realize a solid angle spatial scanning in a horizontal direction and a vertical direction via an electric deflection device connected to the high-voltage generator; and
alternately controlling a vertical propagation direction and a horizontal propagation direction of a charged particle wave emitted by the emission electrode via the electric deflection device, the electric deflection device being connected to the emission electrode, wherein the charged particle wave control unit comprises a waveform storage module, a digital-to-analog conversion module and a power amplification module; and the method for generating the particle wave carrying electric charge further comprises:
generating a digital waveform signal correspondingly according to a pre-stored waveform information in the waveform storage module; and the pre-stored waveform information comprises amplitude and time phase;
converting the digital waveform signal with a pre-set time phase into an analog waveform signal via the digital-to-analog conversion module, wherein the digital-to-analog conversion module is connected to the waveform storage module;
performing a power amplification on the analog waveform signal via the power amplification module, the power amplification module being connected to the digital-to-analog conversion module; and
performing the high-voltage amplification of the power signal of the analog waveform signal via the high-voltage generator, the high-voltage generator being connected to the power amplification module,
wherein the power amplification module comprises a voltage amplifier and a triode,
the voltage amplifier is connected to the digital-to-analog conversion module; and
a base of the triode is connected to the voltage amplifier, a collector of the triode is connected to a power supply, and an emitter of the triode is connected to the high-voltage generator,
wherein the electric deflection device is disposed on one side of the emission electrode, wherein the one side of the emission electrode emits the charged particle wave,
the electric deflection device comprises a vertical voltage waveform high-voltage electrode plate group and a horizontal voltage waveform high-voltage electrode plate group,
the vertical voltage waveform high-voltage electrode plate group is set in the vertical direction while the horizontal voltage waveform high-voltage electrode plate group is set in the horizontal direction,
the vertical voltage waveform high-voltage electrode plate group and the horizontal voltage waveform high-voltage electrode plate group are orthogonal to each other, and are both parallel to an axis of the charged particle emitted by the emission electrode,
the vertical voltage waveform high-voltage electrode plate group and the horizontal voltage waveform high-voltage electrode plate group are respectively configured to control the vertical propagation direction and the horizontal propagation direction of the charged particle wave,
the electric deflection device alternately acts on the charged particle wave emitted by the emission electrode through a pulsed electric fields between plates of the vertical voltage waveform high-voltage electrode plate group and plates of the horizontal voltage waveform high-voltage electrode plate group, and
a propagation direction of the charged particle wave generated is changed by an alternating voltage waveform electric field of the vertical voltage waveform high-voltage electrode plate group and the horizontal voltage waveform high-voltage electrode plate group in the electric deflection device.

8. The method for generating the particle wave carrying electric charge according to claim 7, wherein the generating the digital waveform signal corresponding according to the pre-stored waveform information in the waveform storage module comprises:
- determining an user-selected waveform information according to a plurality of waveform information pre-stored in the waveform storage module, and generating the digital waveform signal correspondingly.

9. The method for generating the particle wave carrying electric charge according to claim 8, wherein the determining the user-selected waveform information comprises:
- receiving a selection instruction sent by an user via a remote controller; and
- determining the user-selected waveform information based on the selection instruction.

10. The method for generating the particle wave carrying electric charge according to claim 7, further comprising:
- determining a working state of the emission electrode according to a state of an indicator lamp.

11. The method for generating the particle wave carrying electric charge according to claim 7, further comprising:
- adopting a fan fixed 2 cm from a front end of the emission electrode, to enlarge a spatial propagation distance and a spatial coverage of the charged particle wave emitted by the emission electrode.

12. The method for generating the particle wave carrying electric charge according to claim 11, wherein
- the charged particle wave control unit further comprises the fan,
- the emission electrode is located between the fan and the electric deflection device, and
- a center of the fan is located on a concentric axis of the emission electrode and the electric deflection device; the plane of the fan is perpendicular to the concentric axis, and the fan is configured to enlarge the spatial propagation distance and the spatial coverage of the charged particle wave emitted by the emission electrode.

13. The method for generating the particle wave carrying electric charge according to claim 7, wherein:
- the vertical voltage waveform high-voltage electrode plate group comprises two voltage waveform high-voltage electrode plates, the two voltage waveform high-voltage electrode plates are oppositely set and parallel to the axis of the charged particle wave emitted by the emission electrode, a distance from the two voltage waveform high-voltage electrode plates of the vertical voltage waveform high-voltage electrode plate group to the emission electrode is d1,
- the horizontal voltage waveform high-voltage electrode plate group comprises two voltage waveform high-voltage electrode plates; the two voltage waveform high-voltage electrode plates are oppositely set and are parallel to the axis of the charged particle wave emitted by the emission electrode, a distance from the two voltage waveform high-voltage electrode plates of the horizontal voltage waveform high-voltage electrode plate group to the emission electrode is d2, and d1 is not equal to d2.

14. The method for generating the particle wave carrying electric charge according to claim 13, wherein each of the voltage waveform high-voltage electrode plate is a square electrode plate,
- the two voltage waveform high-voltage electrode plates of the vertical voltage waveform high-voltage electrode plate group and the two voltage waveform high-voltage electrode plates of the horizontal voltage waveform high-voltage electrode plate group are both parallel to a central axis of the charged particle wave emitted by the emission electrode, and
- a center line respectively spanning between opposing faces of the two voltage waveform high-voltage electrode plates of the vertical voltage waveform high-voltage electrode plate group and the two voltage waveform high-voltage electrode plates of the horizontal voltage waveform high-voltage electrode plate group is perpendicular to a center axis of the emission electrode, the center line being disposed in the direction of the emitted charged particle wave.

15. The method for generating the particle wave carrying electric charge according to claim 13, wherein
- the emission electrode is an annular emission electrode, and
- a distance between the vertical voltage waveform high-voltage electrode plate group and the horizontal voltage waveform high-voltage electrode plate group in the electric deflection device is larger than a diameter of the annular emission electrode.

16. The method for generating the particle wave carrying electric charge according to claim 13, wherein
- the vertical voltage waveform high-voltage electrode plate group is 5 cm away from an emitting end of the emission electrode, and
- the horizontal voltage waveform high-voltage electrode plate group is 2-3 cm away from the emitting end of the emission electrode.

* * * * *